United States Patent
Onodera et al.

(10) Patent No.: US 6,410,786 B1
(45) Date of Patent: Jun. 25, 2002

(54) PROCESS FOR PRODUCING METHACRYLIC ACID

(75) Inventors: Hideo Onodera, Himeji; Naomasa Kimura, Okayama; Eiichi Shiraishi, Himeji, all of (JP)

(73) Assignee: Nippon Shokubai Co, Ltd, Osaka (JP)

( * ) Notice: Subject to any disclaimer, the term of this patent is extended or adjusted under 35 U.S.C. 154(b) by 0 days.

(21) Appl. No.: 09/556,697

(22) Filed: Apr. 24, 2000

(30) Foreign Application Priority Data

Apr. 27, 1999 (JP) ............................................. 11-119170
May 6, 1999 (JP) ............................................. 11-126034

(51) Int. Cl.⁷ ............................................. C07C 51/21
(52) U.S. Cl. ...................................... 562/535; 562/534
(58) Field of Search ................................ 562/532, 534, 562/535

(56) References Cited

U.S. PATENT DOCUMENTS

| | | | |
|---|---|---|---|
| 3,801,634 A | | 4/1974 | Krabetz et al. |
| 3,882,047 A | * | 5/1975 | Niina et al. |
| 3,998,876 A | * | 12/1976 | Kato et al. |
| 3,998,877 A | * | 12/1976 | Oda et al. |
| 4,029,636 A | * | 6/1977 | Lowry et al. |
| 4,042,625 A | * | 8/1977 | Matsuzawa et al. |
| 4,113,768 A | * | 9/1978 | White et al. ................. 562/535 |
| 4,124,634 A | * | 11/1978 | Gotoh et al. |
| 4,261,859 A | * | 4/1981 | Koobiar et al. |
| 4,356,114 A | * | 10/1982 | Kasdowski et al. |
| 4,489,170 A | | 12/1984 | Krabetz et al. |
| 5,206,431 A | | 4/1993 | Hashiba et al. |
| 5,719,318 A | | 2/1998 | Kawajiri et al. |

FOREIGN PATENT DOCUMENTS

EP 0614868 3/1994

OTHER PUBLICATIONS

CA:132: 209794 abs of EP987057 Mar. 2000.*

* cited by examiner

*Primary Examiner*—Jean F. Vollano
(74) *Attorney, Agent, or Firm*—Sherman & Shalloway

(57) ABSTRACT

A process for vapor phase catalytic oxidation of methacrolein to produce methacrylic acid at high yield and with stability over a prolonged period is provided. The process is characterized, in the occasion of producing methacrylic acid by vapor phase catalytic oxidation of methacrolein using a fixed bed shell-and-tube reactor, in that (1) the catalyst layer in each reaction tube is divided into at least two layers in the axial direction of the tube to provide plural reaction zones, and (2) each of the reaction zones is filled with the catalyst in such a manner that the amount of the catalytically active component per unit volume of the reaction tube decreases from the gas inlet portion toward the gas outlet portion.

7 Claims, No Drawings

PROCESS FOR PRODUCING METHACRYLIC ACID

TECHNICAL FIELD TO WHICH THE INVENTION BELONGS

This invention relates to a process for producing methacrylic acid. More particularly, the invention relates to a process for producing methacrylic acid at high yield, through vapor phase catalytic oxidation of methacrolein.

CONVENTIONAL TECHNOLOGY

A large number of proposals have been made in the past concerning the catalysts useful in preparation of methacrylic acid through oxidation of methacrolein with molecular oxygen or molecular oxygen-containing gas, in the presence of an oxidation catalyst. Demands for improvements in activity, selectivity and life of the catalyst, however, have still long been pending.

OBJECT OF THE INVENTION

The object of the present invention is to provide a process which enables production of methacrylic acid through vapor phase catalytic oxidation of methacrolein, at high yield and with stability for a prolonged period.

MEANS TO ACHIEVE THE OBJECT

The reaction to produce methacrylic acid by vapor phase catalytic oxidation of methacrolein using fixed bed shell-and-tube reactor is apt to give rise to such undesirable side reactions as parallel reactions or sequential reactions which reduce selectivity for methacrylic acid and in consequence reduce its yield. The side reactions also provide causes for transfer of used catalyst to undesirable oxidation-reduction condition and clogging of pores in the catalyst, leading to shortening of catalyst life.

We have made concentrative studies how to effectively inhibit such undesirable side-reactions and now discovered that the inhibition could be achieved to improve methacrylic acid yield, by dividing the catalyst layer in each reaction tube into at least two layers to provide plural reaction zones, and filling the catalyst in the reaction zones in such a manner that the amount of the catalytically active component per unit volume of the reaction tube decreases from the gas inlet portion toward the gas outlet portion; and also that whereby catalyst deterioration can be inhibited to allow stable methacrylic acid production at high yield over prolonged period.

Thus, according to the present invention a process for producing methacrylic acid through vapor phase oxidation of methacrolein with molecular oxygen or a molecular oxygen-containing gas sing a fixed bed shell-and-tube reactor filled with catalyst is provided, which is characterized in that (1) the catalyst layer in each reaction tube is divided into at least two layers in the axial direction of the tube to provide plural reaction zones, and (2) the catalyst is filled in the plural reaction zones in such a manner that the amount of the catalytically active component per unit volume of the reaction tube decreases from the gas inlet portion toward the gas outlet portion.

WORKING EMBODIMENT OF THE INVENTION

According to the invention, the catalyst layer in each reaction tube in a fixed bed shell-and-tube reactor to be used in the process is divided into at least two layers to provide plural reaction zones. The more the number of reaction zones, the more effectively prevented are the side reactions, but from industrial standpoint it is economical to provide 2 to 3 reaction zones. The dividing ratio of the reaction zones is variable depending on composition and shape of catalyst to be filled in the reaction zones and cannot be unqualifiedly specified. It can be suitably determined in each individual occasion so as to secure the optimum activity and selectivity as a whole.

According to the present invention, catalyst is filled in the plural reaction zones in such a manner that the amount of the catalytically active component per unit volume of each reaction tube decreases from the gas inlet portion toward the gas outlet portion.

As the catalyst useful in the present invention complex oxides which are expressed by the following general formula (1) and which contain molybdophosphoric acid are conveniently used:

$$Mo_a P_b A_c B_d C_e O_x \qquad (I)$$

wherein Mo is molybdenum; P is phosphorus; A is at least an element selected from the group consisting of arsenic, antimony, germanium, bismuth, zirconium, selenium, cerium, copper, iron, chromium, nickel, manganese, cobalt, tin, silver, zinc, palladium, rhodium and tellurium; B is at least an element selected from the group consisting of vanadium, tungsten and niobium; C is at least an element selected from the group consisting of alkali metals, alkaline earth metals and thallium; and O is oxygen; and a, b, c, d, e and x represent atomic ratios of Mo, P, A, B, C and O, respectively, where when a is 12, b is 0.5–4, c is 0.001–5, d is 0.001–4 and e is 0.001–4 and x is a numerical value determined by degree of oxidation of each of the elements.

Preparation methods and starting materials of the catalyst to be used in the present invention are not critical, but any of the methods and starting materials heretofore generally employed for preparation of this type of catalyst may be used.

Form of use of the catalyst in the present invention again is subject to no critical limitation. Molded catalysts obtained by molding the complex oxide which is expressed by the earlier given general formula (I) and which contains molybdophosphoric acid by any of conventionally practiced methods, such as extrusion molding, tabletting or the like; or carrier-supported catalysts in which the complex oxide is carried on conventionally used carriers such as silicon carbide, α-alumina, silica-alumina, zirconium oxide, titanium dioxide and the like, can be used. Where a carrier-supported catalyst is used, the amount of catalytically active component signifies the weight of the catalyst from which the weight of the carrier is subtracted.

Shape of the catalyst to be used in the present invention again is subject to no critical limitation. Shapes suitable for individual occasion, such as pellets, spheres, rings, tablets and the like can be suitably selected.

Examples of typical means for filling the catalyst in the reaction zones to achieve the reduction in the amount of the catalytically active component per unit volume of the reaction tube from the gas inlet portion toward the gas outlet portion include the following:

1̂ change shape of molded catalyst, e.g., fill the gas inlet portion with pelletized catalyst, and the gas outlet portion, with ring-formed catalyst;

2̂ dilute molded catalyst with inert carrier, e.g., fill the gas inlet portion with undiluted catalyst, and the gas outlet portion, with a mixture of the catalyst with inert carrier;

③ change specific gravity of molded catalyst, e.g., fill the gas inlet portion with catalyst of greater specific gravity, and the gas outlet portion, with the catalyst of less specific gravity which can be readily obtained, for example, by increasing the amount of water used for the preparation of the catalyst;

④ use molded catalyst in combination with carrier-supported catalyst, e.g., fill the gas inlet portion with a molded catalyst and the gas outlet portion, with a carrier-supported catalyst;

⑤ change the amount of catalyst carried on support, e.g., fill the gas inlet portion with a support carrying greater amount of the catalytic component and the gas outlet portion, with that carrying less amount of the catalytic component.

Operation conditions of the vapor phase catalytic oxidation reaction according to the present invention are not critical, but those generally used may be adopted. For example, the vapor phase oxidation reaction can be carried out by introducing a starting gas containing 1–10 volume % of methacrolein, 3–20 volume % of molecular oxygen, 0–60 volume % of steam and 20–80 volume % of inert gas such as nitrogen, carbon dioxide, etc. into the catalyst layers in each reaction tube, and reacting them under such conditions as at temperature ranging from 250–450° C., pressure of 1–10 atmospheres and space velocity (SV) of 300–5000 $hr^{-1}$.

EFFECT OF THE INVENTION

According to the process of the present invention, undesirable side reactions can be effectively inhibited and object methacrylic acid can be produced at high yield.

The inhibition of side reactions also results in reduced catalyst degradation and extension in catalyst life. Thus, object methacrylic acid can be produced at high yield stably over prolonged period.

EXAMPLES

Hereinafter the present invention is explained more specifically, referring to working Examples, in which the conversion, selectivity and one-pass yield were calculated by the following equations.

Conversion (mol %)=(mol number of reacted methacrolein/mol number of supplied methacrolein)×100

Selectivity (mol %)=(mol number of formed methacrylic acid/mol number of reacted methacrolein)×100

One-pass yield (mol %)=(mol number of formed methacrylic acid/mol number of suppled methacrolein)×100

Example 1

Into 40 liters of heated ion-exchange water, 8830 g of ammonium paramolybdate and 531 g of ammonium metavanadate were added and dissolved under stirring. Into this aqueous solution 625 g of orthophosphoric acid (85% by weight), an aqueous solution formed by dissolving 812 g of cesium nitrate in 9 liters of ion-exchange water and 243 g of antimony trioxide powder were added by the order stated, followed by concentration under heating and stirring. Thus obtained slurry was dried for 15 hours at 250° C. and pulverized.

Preparation of Catalyst (1)

Moisture content of the powder formed by above pulverization was adjusted with water and the composition was molded into pellets of each 5 mm in diameter and 6 mm in length with an extrusion-molding machine. The pellets were dried and calcined in an air stream at 400° C. for 3 hours to finish pelletized Catalyst (1). The amount of the active component of Catalyst (1) per unit volume of the reaction tube was about 1.20 g/ml.

Preparation of Catalyst (2)

Moisture content of the powder formed by above pulverization was adjusted with water and the composition was molded into rings of each 5 mm in diameter, 1.5 mm in inner diameter of the trough-hole and 6 mm in length with an extrusion-molding machine.

The rings were dried and thereafter calcined in an air stream at 400° C. for 3 hours to finish ring-formed Catalyst (2). The amount of the active component of Catalyst (2) per unit volume of the reaction tube was about 1.02 g/ml.

The composition of Catalysts (1) and (2) was same as follows in terms of atomic ratios excepting oxygen:

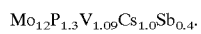

$Mo_{12}P_{1.3}V_{1.09}Cs_{1.0}Sb_{0.4}$.

Oxidation Reaction

The gas inlet portion of a stainless steel reactor of 25.4 mm in inner diameter was filled with 750 ml of Catalyst (1), and the gas outlet portion thereof, with 750 ml of Catalyst (2).

Into the reactor which was filled with the catalyst layers as above, a gaseous mixture obtained through vapor phase catalytic oxidation of isobutylene in the presence of a multi-element catalyst formed of Mo—Bi—Co—W—Fe oxides, i.e., a gaseous mixture composed of

| | |
|---|---:|
| methacrolein | 3.5 vol. % |
| isobutylene | 0.04 vol. % |
| methacrylic acid + acetic acid | 0.24 vol. % |
| steam | 20 vol. % |
| oxygen | 9 vol. % |
| and other components | 67.22 vol. % | was introduced and reacted at a temperature of 290° C. and a space velocity of 1200 $hr^{-1}$. The result was as shown in Table 1.

Comparative Example 1

The reaction was conducted in the same manner as in Example 1, except that 1500 ml of the Catalyst (1) alone, which was obtained in Example 1, was filled in the reactor. The result was as shown in Table 1.

Comparative Example 2

The reaction was conducted in the same manner as in Example 1, except that 1500 ml of the Catalyst (2) alone, which was obtained in Example 1, was filled in the reactor. The result was as shown in Table 1.

Comparative Example 3

The reaction was conducted in the same manner as in Example 1, except that the filling sites of the Catalysts (1) and (2) were reversed from those in Example 1, i.e., the gas outlet portion of the reactor was filled with 750 ml of Catalyst (1) and the gas inlet portion of the reactor, with 750 ml of Catalyst (2). The result was as shown in Table 1.

Example 2

The gas inlet portion of the same reactor to that used in Example 1 was filled with 750 ml of Catalyst (1), and the gas outlet portion, with a mixture of 600 ml of Catalyst (2) with 150 ml of spherical α-alumina of 5 mm in diameter, and the reaction was carried out in the same manner as in Example 1. The result was as shown in Table 1.

Example 3

Preparation of Catalyst (3)

Pellets of each 5 mm in diameter and 6 mm in length were molded in the same manner to the molding of Catalyst (1) except that the amount of water added for adjusting the moisture (content) of the powder for Catalyst (1) was increased to 1.8 times, and the pellets were calcined in an air stream at 400° C. for 3 hours to finish pelletized Catalyst (3). The amount of the active component per unit volume of the reaction tube of this Catalyst (3) was 0.95 g/ml.

Oxidation Reaction

The reaction was carried out in the same manner as in Example 1, the gas outlet portion of the reactor being filled with 750 ml of Catalyst (1) and the gas outlet portion, with 750 ml of Catalyst (3). The result was as shown in Table 1.

Example 4

Preparation of Catalyst (4)

In a slurry formed in the same manner as in Example 1, 1600 ml of spherical α-alumina of 5 mm in diameter was immersed. The system was stirred under heating, whereby having the spherical α-alumina carry the catalytically active component thereon. The carrier-supported type catalyst (4) was finished by calcining it in an air stream at 400° C. for 3 hours. The carried amount of the catalytically active component was 20 g per 100 ml of the catalyst.

The reaction was carried out in the same manner as in Example 1, the gas inlet portion of the reactor being filled with 750 ml of Catalyst (1) and the gas outlet portion, with 750 ml of Catalyst (4). The result was as shown in Table 1.

Example 5

The reaction was carried out in the same manner as in Example 1, except that the gas inlet portion of the reactor was filled with 500 ml of Catalyst (1) and the gas outlet portion, with 1000 ml of Catalyst (2). The result was as shown in Table 1.

Example 6

The reaction was carried out in the same manner as in Example 1, except that the gas inlet portion of the reactor was filled with 1000 ml of Catalyst (1) and the gas outlet portion, with 500 ml of Catalyst (2). The result was as shown in Table 1.

From the results of the reactions as shown in Table 1, it is understood that high selectivity is achieved according to the process of the present invention.

Example 7

The reactions of Examples 1 and 2 and Comparative Example 1 were each carried out continuously for 4000 hours. The results were as shown in Table 2.

From the results of the reactions shown in Table 2, it is understood that catalyst degradation is inhibited according to the process of the present invention.

TABLE 1

|  | Gas Inlet Portion | | | Gas Outlet Portion | | | Performance | | |
| --- | --- | --- | --- | --- | --- | --- | --- | --- | --- |
|  | Catalyst shape | Filled amount of catalyst (ml) | Amount of catalytically active component per unit volume of reaction tube (g/ml) | Catalyst shape | Filled amount of catalyst (ml) | Amount of catalytically active component per unit volume of reaction tube (g/ml) | Methacrolein conversion (mol %) | Methacrylic acid selectivity (mol %) | One-pass yield (mol %) |
| Example 1 | pellet | 750 | 1.20 | ring | 750 | 1.02 | 82.8 | 77.3 | 64.0 |
| Example 2 | pellet | 750 | 1.20 | ring + alumina | 600 | 0.82 | 82.5 | 77.3 | 63.8 |
| Example 3 | pellet | 750 | 1.20 | pellet | 750 | 0.95 | 82.4 | 77.4 | 63.8 |
| Example 4 | pellet | 750 | 1.20 | carrier-supported type | 750 | 0.20 | 81.8 | 78.3 | 64.0 |
| Example 5 | pellet | 500 | 1.20 | ring | 1000 | 1.02 | 82.9 | 77.6 | 64.3 |
| Example 6 | pellet | 1000 | 1.20 | ring | 500 | 1.02 | 83.0 | 77.2 | 64.1 |
| Comparative Example 1 | pellet | 750 | 1.20 | pellet | 750 | 1.20 | 82.6 | 73.9 | 61.0 |
| Comparative Example 2 | ring | 750 | 1.02 | ring | 750 | 1.02 | 82.9 | 75.6 | 62.7 |
| Comparative Example 3 | ring | 750 | 1.02 | pellet | 750 | 1.20 | 82.6 | 74.5 | 61.5 |

TABLE 2

|  | Performance | | |
| --- | --- | --- | --- |
|  | Methacrolein conversion (mol %) | Methacrylic acid selectivity (mol %) | One-pass yield (mol %) |
| Example 1 | 82.3 | 77.6 | 63.9 |
| Example 2 | 82.1 | 77.8 | 63.9 |
| Comparative Example 1 | 81.0 | 74.0 | 59.9 |

What is claimed is:

1. A process for producing methacrylic acid by vapor phase oxidation of methacrolein with molecular oxygen or a molecular oxygen-containing gas using a catalyst-filled, fixed bed shell-and-tube reactor, which is characterized in that
    (1) the catalyst layer in each of the reaction tubes is divided into at least two layers in the axial direction of the tube to provide plural reaction zones and
    (2) the catalyst is filled in the plural reaction zones in such a manner that the amount of the catalytically active component per unit volume of the reaction tube decreases from the gas inlet portion toward the gas outlet portion of the reactor.

2. The process according to claim 1, in which the catalyst is a complex oxide containing molybdophosphoric acid as expressed by general formula (I) below:

$$Mo_a P_b A_c B_d C_e O_x \qquad (I)$$

[where Mo is molybdenum; P is phosphorus; A is at least one element selected from the group consisting of arsenic, antimony, germanium, bismuth, zirconium, selenium, cerium, copper, iron, chromium, nickel, manganese, cobalt, tin, silver, zinc, palladium, rhodium and tellurium; B is at least one element selected from the group consisting of vanadium, tungsten and niobium; C is at least one element selected from the group consisting of alkali metals, alkaline earth metals and thallium; a, b, c, d, e and x denote the atomic ratios of Mo, P, A, B, C and O, respectively, where when a is 12, b is 0.5–4, c is 0.001–5, d is 0.001–4 and e is 0.001–4 and x is a numerical value determined by degree of oxidation of each of the elements.]

3. A process as defined by claim 1 or 2 in which, as a means for filling each of the reaction zones with the catalyst to achieve the decrease in the amount of the catalytically active component per unit volume of the reaction tube from the gas inlet portion toward the gas outlet portion, the gas inlet portion is filled with a pelletized catalyst and the gas outlet portion, with the ring-formed catalyst.

4. A process as defined by claim 1 or 2 in which, as a means for filling each of the reaction zones with the catalyst to achieve the decrease in the amount of the catalytically active component per unit volume of the reaction tube from the gas inlet portion toward the gas outlet portion, the gas inlet portion is filled with a catalyst itself and the gas outlet portion, with a mixture of the catalyst and an inert carrier.

5. A process as defined by claim 1 or 2 in which, as a means for filling each of the reaction zones with the catalyst to achieve the decrease in the amount of the catalytically active component per unit volume of the reaction tube from the gas inlet portion toward the gas outlet portion, the gas inlet portion is filled with a catalyst having a greater specific gravity and the gas outlet portion, with a catalyst of less specific gravity.

6. A process as defined by claim 1 or 2 in which, as a means for filling each of the reaction zones with the catalyst to achieve the decrease in the amount of the catalytically active component per unit volume of the reaction tube from the gas inlet portion toward the gas outlet portion, the gas inlet portion is filled with a molded catalyst and the gas outlet portion, with a carrier-supported catalyst.

7. A process as defined by claim 1 or 2 in which, as a means for filling each of the reaction zones with the catalyst to achieve the decrease in the amount of the catalytically active component per unit volume of the reaction tube from the gas inlet portion toward the gas outlet portion, the gas inlet portion is filled with a carrier-supported catalyst in which a greater amount of the catalyst is carried, and the gas outlet portion, with the carrier-supported catalyst in which a less amount of the catalyst is carried.

* * * * *